US008821710B2

(12) United States Patent
Bhavaraju et al.

(10) Patent No.: US 8,821,710 B2
(45) Date of Patent: Sep. 2, 2014

(54) PRODUCTION OF FUEL FROM CHEMICALS DERIVED FROM BIOMASS

(75) Inventors: Sai Bhavaraju, West Jordan, UT (US); Mukund Karanjikar, West Valley, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 0 days.

(21) Appl. No.: 13/357,463

(22) Filed: Jan. 24, 2012

(65) Prior Publication Data

US 2012/0123168 A1 May 17, 2012

Related U.S. Application Data

(60) Provisional application No. 61/577,496, filed on Dec. 19, 2011, provisional application No. 61/436,088, filed on Jan. 25, 2011.

(51) Int. Cl.
*C25B 3/00* (2006.01)
*C25B 3/02* (2006.01)
*C25B 3/10* (2006.01)
*C07C 51/41* (2006.01)
*C07C 51/00* (2006.01)
*C07C 51/09* (2006.01)
*C25B 9/08* (2006.01)

(52) U.S. Cl.
CPC . *C07C 51/00* (2013.01); *C25B 3/02* (2013.01); *C07C 51/412* (2013.01); *C07C 51/09* (2013.01); *C07C 51/41* (2013.01); *C25B 9/08* (2013.01)
USPC ............ 205/446; 205/449; 205/455; 205/462

(58) Field of Classification Search
CPC ................ C25B 3/00; C25B 3/02; C25B 3/10
USPC .................................. 205/446, 449, 455, 462
See application file for complete search history.

(56) References Cited

U.S. PATENT DOCUMENTS 2,760,926 A 8/1956 Kronenthal
2,867,569 A * 1/1959 Kronenthal ................... 205/452

(Continued)

FOREIGN PATENT DOCUMENTS

CN 101089231 12/2007
CN 101336313 12/2008

(Continued)

OTHER PUBLICATIONS

Pande et al., "Studies on Kolbe's Electrosynthesis", Electrochimica Acta (Aug. 1961), vol. 4, pp. 215-231.*

(Continued)

*Primary Examiner* — Edna Wong
(74) *Attorney, Agent, or Firm* — David Fonda

(57) ABSTRACT

Hydrocarbons may be formed from six carbon sugars. This process involves obtaining a quantity of a hexose sugar. The hexose sugar may be derived from biomass. The hexose sugar is reacted to form an alkali metal levulinate, an alkali metal valerate, an alkali metal 5-hydroxy pentanoate, or an alkali metal 5-alkoxy pentanoate. An anolyte is then prepared for use in a electrolytic cell. The anolyte contains the alkali metal levulinate, the alkali metal valerate, the alkali metal 5-hydroxy pentanoate, or the alkali metal 5-alkoxy pentanoate. The anolyte is then decarboxylated. This decarboxylating operates to decarboxylate the alkali metal levulinate, the alkali metal valerate, the alkali metal 5-hydroxy pentanoate, or the alkali metal 5-alkoxy pentanoate to form radicals, wherein the radicals react to form a hydrocarbon fuel compound.

6 Claims, 13 Drawing Sheets

(56) References Cited

U.S. PATENT DOCUMENTS

| | | | |
|---|---|---|---|
| 3,992,471 A | 11/1976 | Turolla | |
| 3,994,471 A | 11/1976 | Turolla | |
| 4,006,065 A | 2/1977 | Meresz et al. | |
| 4,123,336 A | 10/1978 | Seko et al. | |
| 4,402,804 A | 9/1983 | Jackson | |
| 4,464,236 A | 8/1984 | Noding | |
| 5,084,146 A | 1/1992 | Huang | |
| 5,290,405 A * | 3/1994 | Joshi et al. | 205/338 |
| 5,580,430 A | 12/1996 | Balagopal et al. | |
| 5,633,400 A | 5/1997 | Wagner et al. | |
| 5,841,002 A * | 11/1998 | Harrison et al. | 568/853 |
| 5,892,107 A * | 4/1999 | Farone et al. | 562/515 |
| 6,193,872 B1 | 2/2001 | Reason et al. | |
| 6,238,543 B1 | 5/2001 | Law et al. | |
| 6,362,380 B1 | 3/2002 | Eicken et al. | |
| 6,392,091 B2 | 5/2002 | Lin | |
| 2001/0019020 A1* | 9/2001 | Merk et al. | 205/413 |
| 2005/0177008 A1 | 8/2005 | Balagopal et al. | |
| 2008/0177114 A1 | 7/2008 | Goossen et al. | |
| 2008/0245671 A1 | 10/2008 | Balagopal et al. | |
| 2009/0074611 A1 | 3/2009 | Monzyk et al. | |
| 2009/0305942 A1 | 12/2009 | Day et al. | |
| 2010/0159553 A1* | 6/2010 | Bradin | 435/167 |
| 2010/0258447 A1* | 10/2010 | Fan | 205/413 |
| 2010/0331170 A1 | 12/2010 | Balagopal et al. | |
| 2011/0024288 A1 | 2/2011 | Bhavaraju et al. | |
| 2011/0027848 A1 | 2/2011 | Karanjikar et al. | |
| 2011/0111475 A1* | 5/2011 | Kuhry et al. | 435/166 |
| 2011/0168569 A1 | 7/2011 | Bhavaraju et al. | |
| 2011/0226633 A1 | 9/2011 | Bhavaraju et al. | |
| 2012/0031769 A1 | 2/2012 | Bhavaraju et al. | |
| 2012/0142945 A1 | 6/2012 | Hwang et al. | |
| 2013/0001095 A1* | 1/2013 | Bhavaraju et al. | 205/340 |
| 2013/0186770 A1 | 7/2013 | Mosby et al. | |

FOREIGN PATENT DOCUMENTS

| | | |
|---|---|---|
| JP | 06271499 | 9/1994 |
| SU | 979325 | 12/1982 |
| WO | WO-2007/095215 | 8/2007 |

OTHER PUBLICATIONS

Schafer, Recent Contributions of Kolbe Electrolysis to Organic Synthesis, Topics in Current Chemistry (© no month, 1990), vol. 152, pp. 92-151.*
Bozell, "Connecting Biomass and Petroleum Processing with a Chemical Bridge", Science (Jul. 30, 2010), vol. 329, pp. 522-523.*
Schafer, "Recent Contributions of Kolbe Electrolysis to Organic Synthesis," Topics in Current Chemistry (© no month, 1990), vol. 152, pp. 92-151.*
Conway, et al., "New Approaches to the Study of Electrochemical Decarboxylation and the Kolbe Reaction. I. The Model Reaction with Formate", *Canadian Journal of Chemistry* (no month, 1963), vol. 41, (1963),21-37.
Wong, Edna Final Office Action, U.S. Appl. No. 12/840,913, (Aug. 14, 2012),1-28.
Palit, Santi R., "The Solubility of Soaps and of Some Salts in Mixtures of Solvents, One of Which Is of Glycolic Type", *Utah Consortia UALC*, vol. 69, (Dec. 1947),3120-29.
Park, Sang Ho PCT International Search Report, Int. App. No. PCT/US2010/042715, (Apr. 29, 2011),1-3.
Park, Sang Ho PCT Written Opinion, Int. App. No. PCT/US2010/042715, (Apr. 29, 2011),1-4.
Kang, Sang Yoon PCT International Search Report, Int. App. No. PCT/US2010/042756, (Feb. 28, 2011),1-3.
Kang, Sang Yoon PCT Written Opinion, Int. App. No. PCT/US2010/042756, (Feb. 28, 2011),1-4.
Park, Sang Ho PCT International Search Report, Int. App. No. PCT/US2010/042780, (May 2, 2011),1-3.
Park, Sang Ho PCT Written Opinion, Int. App. No. PCT/US2010/042780, (May 2, 2011),1-4.
Bozell, Joseph J., "Connecting Biomass and Petroleum Processing with a Chemical Bridge", *Science*, (Jul. 30, 2010),vol. 329: 522-523.
Bond, Jesse Q., et al., "Integrated Catalytic Conversion of gamma-Valerolactone of Liquid Alkenes for Transportation Fuels", *Science*, (Feb. 26, 2010),vol. 327: 1110-1114.
Chum, H L., et al., "Photoelectrochemistry of Levulinic Acid on Undoped Platinized n-TIO2 Powders", *J. Phys. Chem*, (1983),vol. 87: 3089-3093.
Schafer, Hans-Jurgen "Recent Contributions of Kolbe Electrolysis to Organic Synthesis", *Topics in Current Chemistry*, (1990),vol. 152: 91-151.
Rabjohn, et al., "Kolbe Electrosynthesis of Alkanes with Multiple Quaternary Carbon Atoms", *J. Org. Chem.*, (1981),vol. 46, pp. 4082-4083.
Wong, Edna USPTO Office Action, U.S. Appl. No. 12/840,508, (Nov. 2, 2011),17 pages.
Kobzeva, et al., "Effect of a solvent on anode processes", *Elektrokhimiya*, vol. 11. No. 5, (1975),1 page abstract.
Ono, et al., "Electrolysis of fatty acids I", *Ind. Chem. Sect.* 53, (1950),1 page abstract.
Minami, et al., "Electrolysis of Fatty Acids II", *Kogyo Kagaku Zasshi*, vol. 53, (1950),1 page abstract.
Obermuller, "Saponification by Sodium Ethoxide", *J Chem. Soc.*, Abstr. 62, (1892),1 page abstract.
Wong, Edna USPTO Office Action, U.S. Appl. No. 12/840,913, (Nov. 16, 2011),16 pages.
Wong, Edna Non-Final Office Action, U.S. Appl. No. 12/840,508, (Apr. 26, 2012),1-32.
Wong, Edna Non-Final Office Action, U.S. Appl. No. 12/840,913, (Apr. 10, 2012),1-12.
Mendez, Zulmariam Non-Final Office Action, U.S. Appl. No. 12/840,401, (Jun. 5, 2012),1-12.
Ho, Park S., International Search Report, PCT US 2011/035782 (corresponding to U.S. Appl. No. 13/103,716, (Feb. 9, 2012),1-3.
Ho, Park S., Written Opinion of the International Searching Authority, PCT US 2011/035782 (corresponding to U.S. Appl. No. 13/103,716, (Feb. 9, 2012),1-4.
Ko, et al., Computer Translation of the Detailed Description of JP 6-271499, Japanese Patent publication 06-271499, (Sep. 27, 1994),1-8.
Aslanov, N. N. "English Language Bibliographical Information and Abstract", SU Patent No. 979325, (Dec. 7, 1982),1-3.
Choi, et al., "Recovery of lactic acid from sodium lactate by ion substitution using ion-exchange membrane", *Separation and Purification Technology* 28 (2002), Elsevier, (Mar. 4, 2002),69-79.
Habova, et al., "Application of Electrodialysis for Lactic Acid Recovery", *Czech J. Food Sci.*, vol. 19, No. 2 (2001), (Jan. 1, 2001),73-80.
Huang, et al., "Application of electrodialysis to the production of organic acids: State-of-the-art and recent developments", *Journal of Membrane Science* 288 (2007), Elsevier, (Nov. 25, 2006),1-12.
Lu, et al., "Modeling of the mass transfer and conduction behavior in electro-electrodialysis with oil/water emulsion as the catholyte", *Journal of Membrane Science* 322 (2008), Elsevier, (Jun. 5, 2008),265-274.
Moon, et al., "Competitive Anion Transport in Desalting Mixtures of Organic Acids by Batch Electrodialysis", *Journal of Membrane Science* 141 (1998), Elsevier, (Apr. 1, 1998),75-89.
Palaty, et al., "Continuous dialysis of carboxylic acids. Permeability of Neosepta-AMH membrane", *Desalination* 216 (2007), Elsevier, (Oct. 1, 2007),345-355.
Prado Rubio, et al., "Modeling Reverse Electro-Enhanced Dialysis for Integration with Lactic Acid Fermentation", *CAPEC, Department of Chemical and Biochemical Engineering Technical University of Denmark (DTU)*, DK-2800 Lyngby, Denmark, 2009, Available as "A-DK-Prado Rubio-OA-1" at Docstoc.com, http://www.docstoc.com/search/modeling%20reverse%20electro~
enhanced%20dialysis%20for%20integration%20with%20lactic
%20acid%20fermentation?catid=0,(Jan. 1, 2009),1-2.
Yi, et al., "An in situ coupling separation process of electro-electrodialysis with back-extraction", *Journal of Membrane Science* 255 (2005), Elsevier, (Mar. 21, 2005),57-65.
Wong, Edna Final Office Action, U.S. Appl. No. 12/840,508, (Nov. 27, 2012),1-25.

(56) References Cited

OTHER PUBLICATIONS

Park, Sang H., International Search Report, PCT Application No. PCT/US2011/033626 (corresponding to U.S. Appl. No. 13/092,685, (Feb. 8, 2012),1-3.

Park, Sang H., Written Opinion of the International Searching Authority, PCT Application No. PCT/US2011/033626 (corresponding to U.S. Appl. No. 13/092,685, (Feb. 8, 2012),1-4.

Paul, et al., "Reactions of Sodium Metal with Aromatic Hydrocarbons", *J. Am. Chem. Soc.,* 1956, 78 (1), (Jan. 1956),116-120.

Dzik, et al., "Carboxylates as sources of carbon nucleophiles and electrophiles: comparison of decarboxylative and decarbonylative pathways", *Chemical Science,* 2012, vol. 3, Issue No. 9 (2012), (May 3, 2012),2671-78.

Mendez, Zulmariam Final Office Action, U.S. Appl. No. 12/840,401, (Mar. 15, 2013),1-12.

Mendez, Zulmariam Non Final Office Action, U.S. Appl. No. 12/840,401, (Jul. 30, 2013),1-15.

Wong, Edna Final Office Action, U.S. Appl. No. 12/840,913, (Jul. 18, 2013),1-16.

Wong, Edna Notice of Allowance, U.S. Appl. No. 12/840,508, (Apr. 29, 2013),1-11.

Shafer, Hans J., "Electrochemical Conversion of Fatty Acids", *European Journal of Lipid Science and Technology,* vol. 114, Issue 1, (Oct. 11, 2011),2-9.

Wong, Edna Non Final Office Action, U.S. Appl. No. 12/840,913, (Mar. 28, 2013),1-31.

Sekine, Isao et al., "Effect of the Concentration of Acetate or Propionate on the Abnormal Phenomena in the Kolbe Reaction", *Denki Kagaku,* vol. 41(9), (1973),702-707.

Stapley, et al., English Language Abstract, CN101336313A, (Dec. 31, 2008),1.

Hongyou, et al., English Language Abstract, CN101089231A, (Dec. 19, 2007),1.

Le, Zhikang Chinese Office Action, Chinese Application No. 201080024541.8, (Jan. 21, 2014),1-10.

Mendez, Zulmariam Non-Final Office Action, U.S. Appl. No. 13/790,744, (Mar. 20, 2014),1-22.

Mendez, Zulmariam Final Office Action, U.S. Appl. No. 12/840,401, (Mar. 13, 2014),1-23.

Wong, Edna Non-Final Office Action, U.S. Appl. No. 13/612,192, (Apr. 8, 2014),1-24.

Wong, Enda Notice of Allowance, U.S. Appl. No. 12/840,913, (Oct. 4, 2013),1-11.

Wong, Edna Non-Final Office Action, U.S. Appl. No. 13/612,192, (Dec. 10, 2013),1-33.

* cited by examiner

PRODUCTION OF FUEL FROM CHEMICALS DERIVED FROM BIOMASS

CROSS-REFERENCE TO RELATED APPLICATIONS

This application claims the benefit of U.S. Provisional Patent Application Ser. No. 61/577,496 filed Dec. 19, 2011, entitled "Decarboxylation of Levulinic Acid to Make Solvent." This application also claims the benefit of U.S. Provisional Patent Application Ser. No. 61/436,088 filed Jan. 25, 2011, entitled "Production of Fuel from Chemicals Derived from Biomass." Both of these provisional applications are expressly incorporated herein by reference.

BACKGROUND OF THE INVENTION

Hydrocarbon fuels are currently used throughout the world. One specific example of a hydrocarbon fuel is gasoline (which includes octane). Another common hydrocarbon fuel is diesel fuel, which is used in diesel engines. Accordingly, there is a need for methods for producing hydrocarbons that may be used as fuels.

Biomass is a renewable feedstock. Biomass may comprise lipids (such as fats or oils) that are available from plant, algal, or animal origin. These fats or oils may include fatty acids. Obviously, given its abundance in nature, it is desirable to find a way to use this biomass as a starting material to form a useable product, such as a hydrocarbon fuel.

Current methods to convert biomass to a hydrocarbon fuel involve the process known as "hydroreacting" in which hydrogen gas is added to the biomass (in the presence of a catalyst) to convert the biomass to hydrocarbons. Unfortunately, hydroreacting is generally expensive because hydrogen gas is an expensive reactant. Also, a catalyst is involved in this process, and such catalysts are often intolerant with Ca, Cl, V, N, As, Hg, Si, P, Cr or other materials that may be found in the biomass. Other impurities include soluble vitamins, steroids, terpenes, alkaloids, etc. Another process to convert biomass to hydrocarbons is decarboxylation, wherein the carboxylic acid functionality of a fatty acid is "decarboxylated," thereby leaving a hydrocarbon. (In some situations, this decarboxylation step may be preceded by a fermentation step and/or a hydrolysis step, depending upon the starting material.) Employing the decarboxylation process to produce the hydrocarbon is generally expensive.

Accordingly, there is a need for a new process by which biomass may be converted into a hydrocarbon. Such a process is disclosed herein.

BRIEF SUMMARY OF THE INVENTION

Disclosed herein is a method for the manufacture of hydrocarbon fuels from biomass. This method relates to the conversion of the biomass based starting materials such as carbohydrates and sugars, to carboxylic acids or alkali metal salts of carboxylic acids (and other carboxylic acid derivatives such as esters) that may be used to form hydrocarbon fuels. Also disclosed are methods for turning biomass into lactones that may also be converted into hydrocarbon fuels. The biomass can be of plant, algal, or animal origin.

In the present method, the biomass is converted to sugars (mainly hexoses that include one or more rings). These hexose sugars will generally have 6 carbon atoms which in turn are chemically converted to carboxylic acids. Examples of these types of sugar materials include glucose, etc. Specifically, a sugar monomer, which has the formula $C_6H_{12}O_6$, may be reacted as follows to form levulinic acid, water and formic acid:

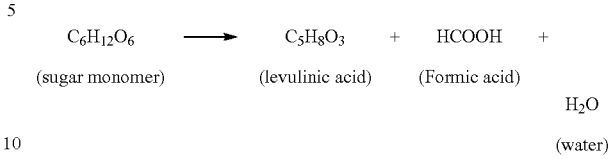

$C_5H_8O_3$ is the empirical formula of levulinic acid. However, this acid has the following chemical structure:

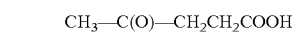

Once these two acids (levulinic acid and formic acid) are obtained, these two acids may be saponified by reaction with a base (such as NaOH, NaOCH$_3$, or any other base) to form the corresponding alkali metal salt (e.g., alkali metal salts of formate and levulinate):

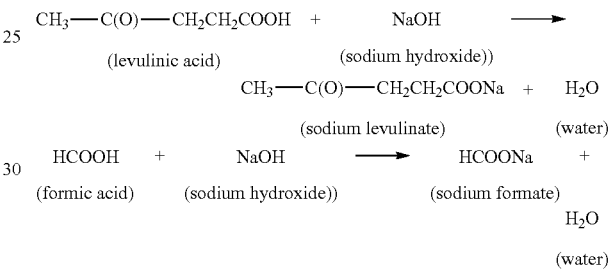

Alternatively, the sugars are directly converted to alkali salts of carboxylic acids.

These alkali salts of carboxylic acids are then dissolved in a solvent and optionally with a second alkali carboxylate to yield a reacting mixture. The mixture is then converted to hydrocarbon fuel by electrolytic (anodic) decarboxylation and subsequent carbon-carbon coupling. The electrolysis cell deployed for this reaction utilizes a selective alkali transport solid electrolyte membrane technology. The product formed by this carbon-carbon coupling may be a hydrocarbon fuel material—e.g., a hydrocarbon that may be used as a fuel, a fuel additive, etc.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the present embodiments, as represented in the Figures, is not intended to limit the scope of the invention, as claimed, but is merely representative of presently preferred embodiments of the invention.

Figure 1:
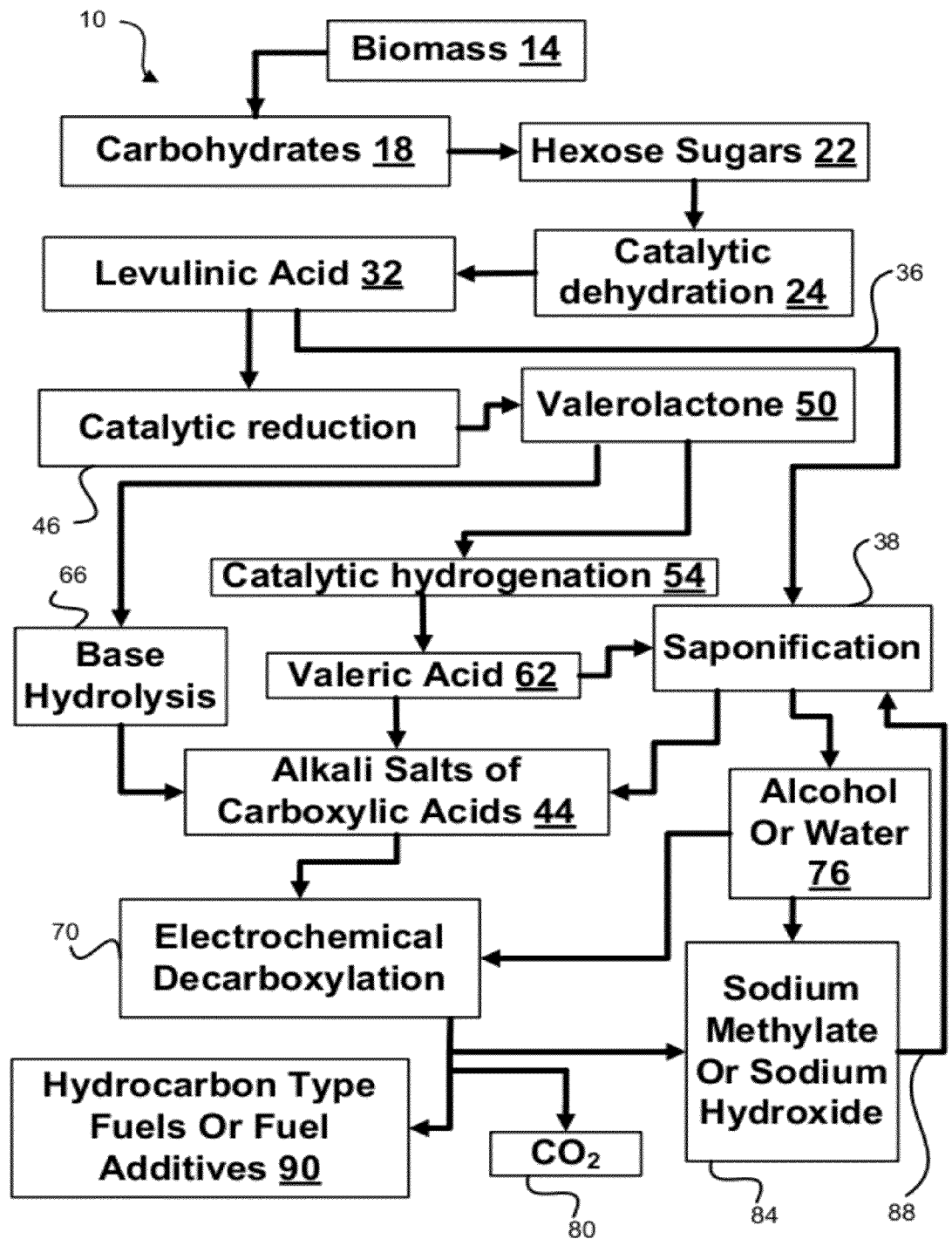
FIG. 1 is a flow diagram showing the overall process by which biomass may be converted into hydrocarbon fuels.

Referring now to FIG. 1, a flow diagram which shows the method 10 in which biomass 14 may be converted into a hydrocarbon according to the process outlined herein. For example, a quantity of biomass 14 is obtained. The biomass 14 may then be converted into a carbohydrate 18. This carbohydrate 18 may be a starch material, a cellulose material, a polysaccharide material, etc. This process for converting the biomass 14 into the carbohydrate 18 is known. After a carbohydrate 18 has been obtained, the carbohydrate 18 may be converted into a hexose sugar material 22 (such as glucose, etc.). The conversion of the carbohydrate material 18 into a hexose sugar material 22 may occur via chemical hydrolysis or enzymatic hydrolysis. Such processes are known and are described, for example, in the following article:

Fan et. al., "Cellulose Hydrolysis," Biotechnology Monographs, Vol. 3, Springer NY, 1987.

After obtaining the hexose sugar material 22, this material 22 may undergo a catalytic dehydration 24 (or other process) to convert the sugar moieties into levulinic acid 32. The process for converting a hexose sugar into levulinic acid is described, for example, in the following article:

Bozell J., Connecting Biomass and Petroleum Processing with a Chemical Bridge, Science, Vol. 239, pp 522-523, (2010).

This process is a dehydration reaction as water is produced. Formic acid may also be produced during this reaction. The ratio of levulinic acid 32 to formic acid that is produced in this reaction may be approximately a 3:1 weight ratio. (Water is also formed during this process.) This transformation has been known for decades. Accordingly, those skilled in the art are familiar with the processes needed to create levulinic acid. Further information regarding the production of levulinic acid is found in the following article:

Bond, Jesse Q., et al., Integrated Catalytic Conversion of γ-Valerolactone to Liquid Alkenes for Transportation Fuels, Science 327, 1110-1114 (2010).

The reaction of the hexose sugar to levulinic acid ($CH_3CO(CH_2)_2COOH$) is summarized as follows:

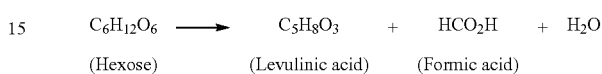

As shown by arrow 36, the levulinic acid 32 may undergo a saponification reaction 38 to produce an alkali salt of a carboxylic acid 44. More specifically, this alkali salt of a carboxylic acid may be the alkali metal salt of levulinic acid (e.g., an alkali metal levulinate). The saponification reaction 38 uses a base (such as an alkali metal methoxide or an alkali metal hydroxide).

Additionally or alternatively, the levulinic acid 32 may undergo a catalytic reduction process 46 to gamma-valerolactone 50 (γ-valerolactone). This gamma-valerolactone 50 (a cyclic ester) is produced by catalytic hydrogenation:

In turn, this γ-valerolactone 50 may undergo a catalytic hydrogenation reaction 54 to produce valeric acid 62:

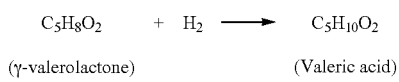

This valeric acid 62 can undergo the saponfication reaction 38 to form the alkali salt of a carboxylic acid 44. (In this case, the alkali salt of a carboxylic acid would be the alkali metal valerate.) Alternatively, the γ-valerolactone 50 may undergo a base hydrolysis process 66 to form the alkali salt of a carboxylic acid 44. This hydrolysis reaction of the cyclic ester (γ-valerolactone) uses a base (alkali methoxide or alkali hydroxide) to form an ether or an alcohol. This reaction is shown below using sodium as the alkali cation:

The reaction of the alkali salt of a carboxylic acid 44 will now be described. The alkali salt of a carboxylic acid 44 may be used in an electrochemical cell. As will be described in detail herein, the electrochemical cell produces a decarboxylation reaction 70 using a sodium conductive membrane. (An alcohol or water material 76 is used in this electrochemical reaction.) This electrochemical reaction 70 produces a quantity of carbon dioxide 80 as well as a quantity of base 84. This base 84 may be sodium hydroxide, sodium methoxide, sodium methylate, etc. (In turn, this quantity of base 84 may be reused in the saponification reaction 38, as shown by arrow 88.) The electrochemical reaction 70 also produces a hydrocarbon 90. This hydrocarbon may be a hydrocarbon fuel or other similar chemical that may be used as a fuel additive. (This process will be described in greater detail herein).

Figure 2A:
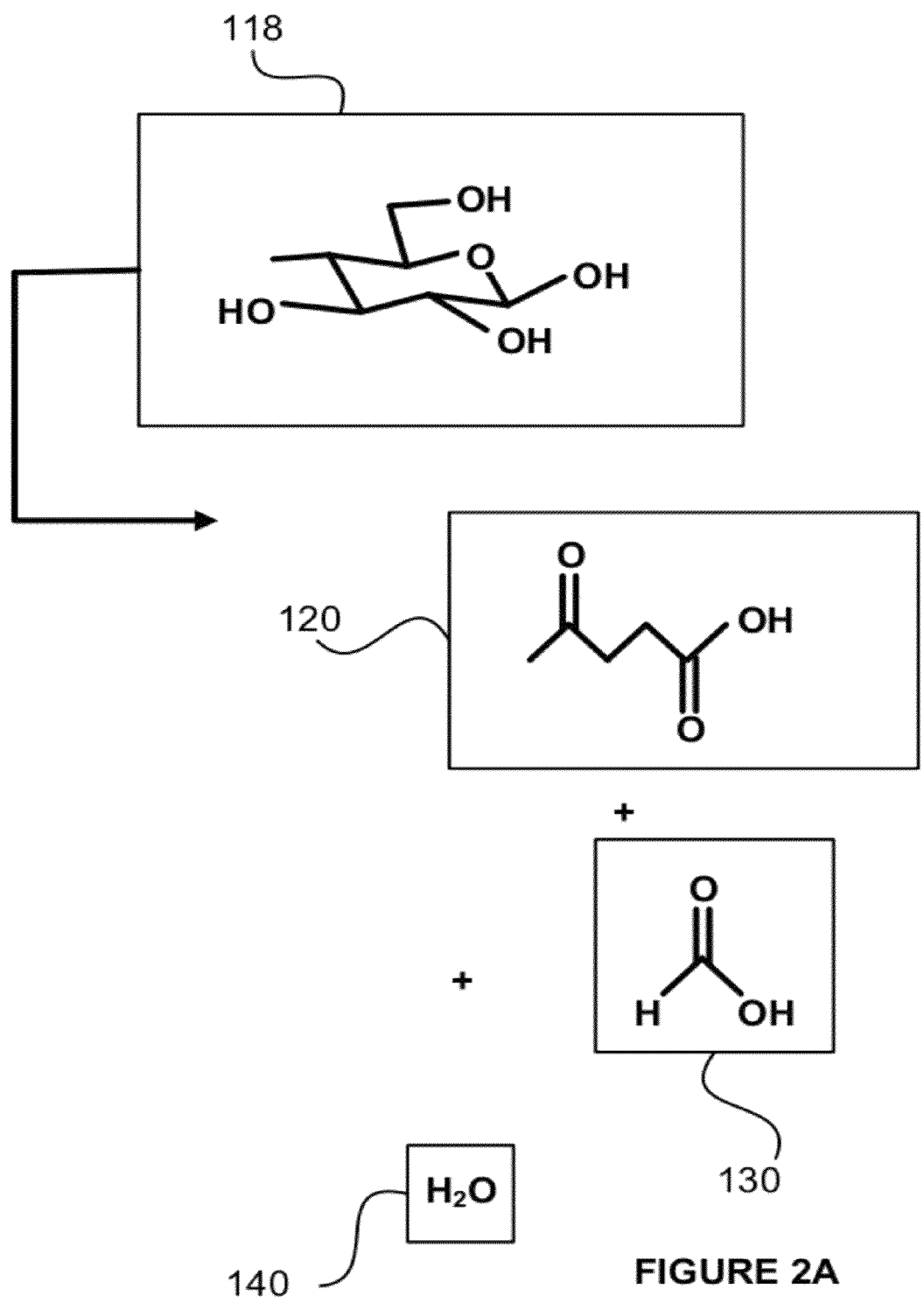
FIG. 2A is a flow diagram showing the conversion of sugar moieties into levulinic acid and formic acid.

Referring now to FIG. 2A, the process for converting sugar moieties into levulinic acid is described. Specifically, this process may involve converting a hexose sugar 118 (such as glucose, etc.) into levulinic acid. This process is a dehydration reaction as water 140 is produced. The dehydration of a sugar 118, which is performed by treatment with acid, ultimately forms levulinic acid 120 and formic acid 130.

Figure 2B:
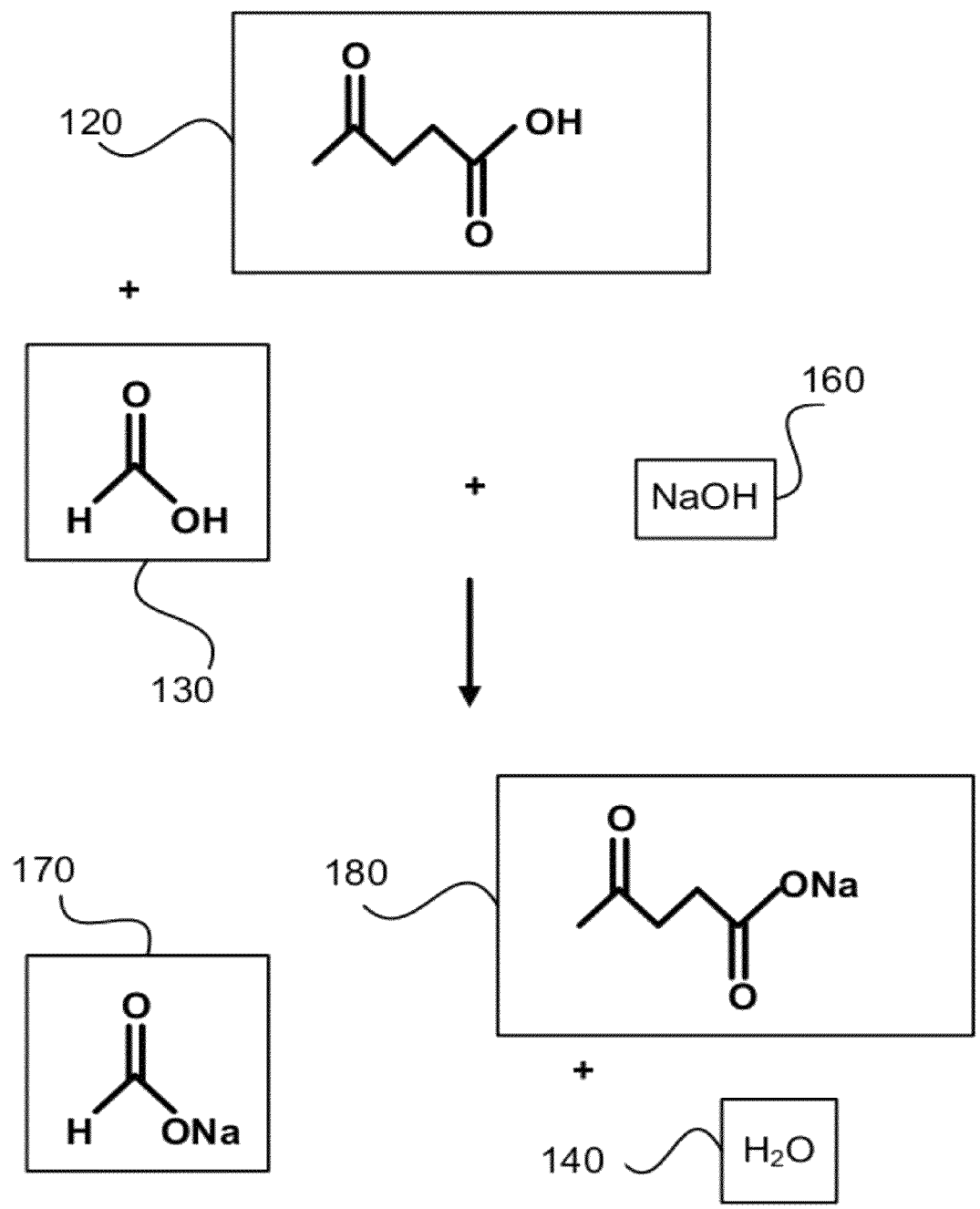
FIG. 2B is a flow diagram showing the conversion of levulinic acid and formic acid to sodium formate and sodium levulinate.

Referring now to FIG. 2B, the saponification reaction of levulinic acid is described. (Those skilled in the art will appreciate that a similar saponification reaction may occur using valeric acid.) The saponification reaction involves reacting levulinic acid 120 and/or the formic acid 130 with a base 160. In FIG. 2B, the base 160 is NaOH. However, other bases may be used (such as sodium methoxide, sodium ethoxide, KOH, potassium methoxide, etc.) This saponification reaction produces water 140, sodium formate 170 and sodium levulinate 180. Of course, instead of sodium, another alkali metal may be used as the corresponding cation. These saponfication reactions can be summarized as follows (with sodium as the alkali metal cation):

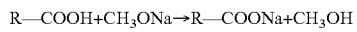

R—COOH+CH$_3$ONa→R—COONa+CH$_3$OH

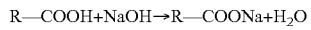

R—COOH+NaOH→R—COONa+H$_2$O

Where, R is the remaining section of levulinic or valeric acids.

The chemical reactions that occur in the electrochemical cell will now be described. Specifically, the alkali metal salt of the acid (such as, for example R—COONa (or the carboxylate with additional ether or alcohol functional group)) may be separated and used to prepare an anolyte for an electrochemical cell. This anolyte may further include a solvent and optionally a second sodium carboxylate.

The anolyte may then be fed into an electrolytic cell that uses a sodium ion conductive ceramic membrane that divides the cell into two compartments: an anolyte compartment and a catholyte compartment. The electrolytic cell may be of standard parallel plate cell where flat plate electrodes and membranes are used or of tubular type cell where tubular electrodes and membranes are used. An electrochemically active first anode (e.g. smooth platinum, stainless steel, metal alloy anodes e.g. Kovar, carbon based electrodes such as boron doped diamond, glassy carbon, synthetic carbon, Dimensionally Stable Anodes (DSA), lead dioxide) that allow the desired reaction to take place) is housed in the first anolyte compartment where oxidation (decarboxylation) reaction and subsequent free radical carbon-carbon coupling takes place.

At the anode of the electrochemical cell, various reactions may occur. One type of these reactions is referred to as the "Kolbe reaction." This reaction involves an oxidation (decarboxylation) step. Specifically, in the standard Kolbe reaction, anodic decarboxylation/oxidative coupling of carboxylic acids occurs. This reaction is a free radical reaction and is shown below:

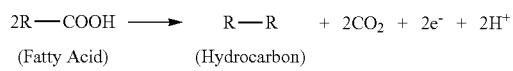

2R—COOH → R—R + 2CO$_2$ + 2e$^-$ + 2H$^+$
(Fatty Acid)    (Hydrocarbon)

This Kolbe reaction is typically conducted in non-aqueous methanolic solutions, with partially neutralized acid (in the form of alkali salt) used with a parallel plate type electrochemical cell. The anolyte used in the cell may have a high density. The Kolbe reaction has been known and used. In fact, the following article summarizes and explains the Kolbe reaction:

Hans-Jurgen Schafer, Recent Contributions of Kolbe electrolysis to organic synthesis, Topics in Current Chemistry, Vol. 153, Issue: Electrochemistry IV, 1990, pp. 91-151.

As can be seen from the Kolbe reaction, the "R" groups of two fatty acid molecules are coupled together, thereby resulting in a hydrocarbon product. The Kolbe reaction is a free radical reaction in which two "R radicals" (R.) are formed and are subsequently combined together to form a carbon-carbon bond.

The present embodiments relate to a modified "Kolbe" reaction. Specifically, the present embodiments involve decarboxylation to form an "R radical" (R.) These radical species may couple together to form hydrocarbon products.

As noted above, sodium levulinate may be decarboxylated at the anode of a cell to produce a radical. This reaction may be represented as follows:

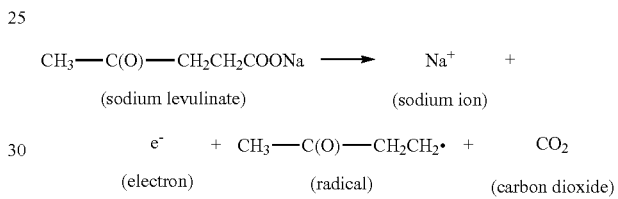

CH$_3$—C(O)—CH$_2$CH$_2$COONa  →  Na$^+$  +
(sodium levulinate)                    (sodium ion)

e$^-$  +  CH$_3$—C(O)—CH$_2$CH$_2$•  +  CO$_2$
(electron)        (radical)                (carbon dioxide)

If formate is present in the anolyte, the formate may also react as follows:

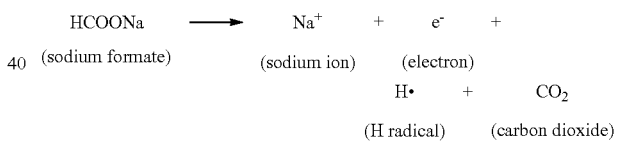

HCOONa  →  Na$^+$  +  e$^-$  +
(sodium formate)    (sodium ion)   (electron)
                                H•  +  CO$_2$
                          (H radical)  (carbon dioxide)

Thus, when a solution containing formate and levulinate are decarboxylated together, the H radicals and the other radicals may react together to form a variety of species, including hydrocarbons. The above decarboxylation reactions are typically conducted in non-aqueous solutions at high current densities. When the carboxylate is sodium levulinate (CH$_3$CO(CH$_2$)$_2$COONa), the product obtained is CH$_3$CO(CH$_2$)$_4$COCH$_3$. More specifically, this radical reaction occurs as follows:

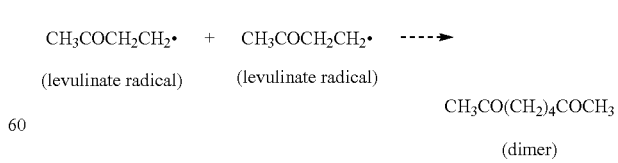

CH$_3$COCH$_2$CH$_2$•  +  CH$_3$COCH$_2$CH$_2$•  ---→
(levulinate radical)    (levulinate radical)

CH$_3$CO(CH$_2$)$_4$COCH$_3$
(dimer)

This dimer product is very similar to octane and could be used as an additive to gasoline. When the carboxylate is sodium valerate (CH$_3$(CH$_2$)$_3$COONa), the product is octane, CH$_3$(CH$_2$)$_6$CH$_3$, the primary component gasoline.

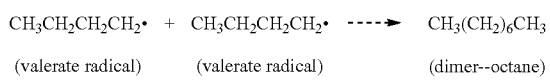

In a similar manner, when the carboxylate is CH$_3$O—C$_4$H$_8$—COONa (e.g., a CH$_3$ONa hydrolysis product of γ-valerolactone), the product obtained is CH$_3$O(CH$_2$)$_8$OCH$_3$. When the carboxylate is HO—C$_4$H$_8$—COONa (e.g., a NaOH hydrolysis product of γ-valerolactone), the product obtained is HO(CH$_2$)$_8$OH. These products could be used as additives to gasoline.

Figure 3:
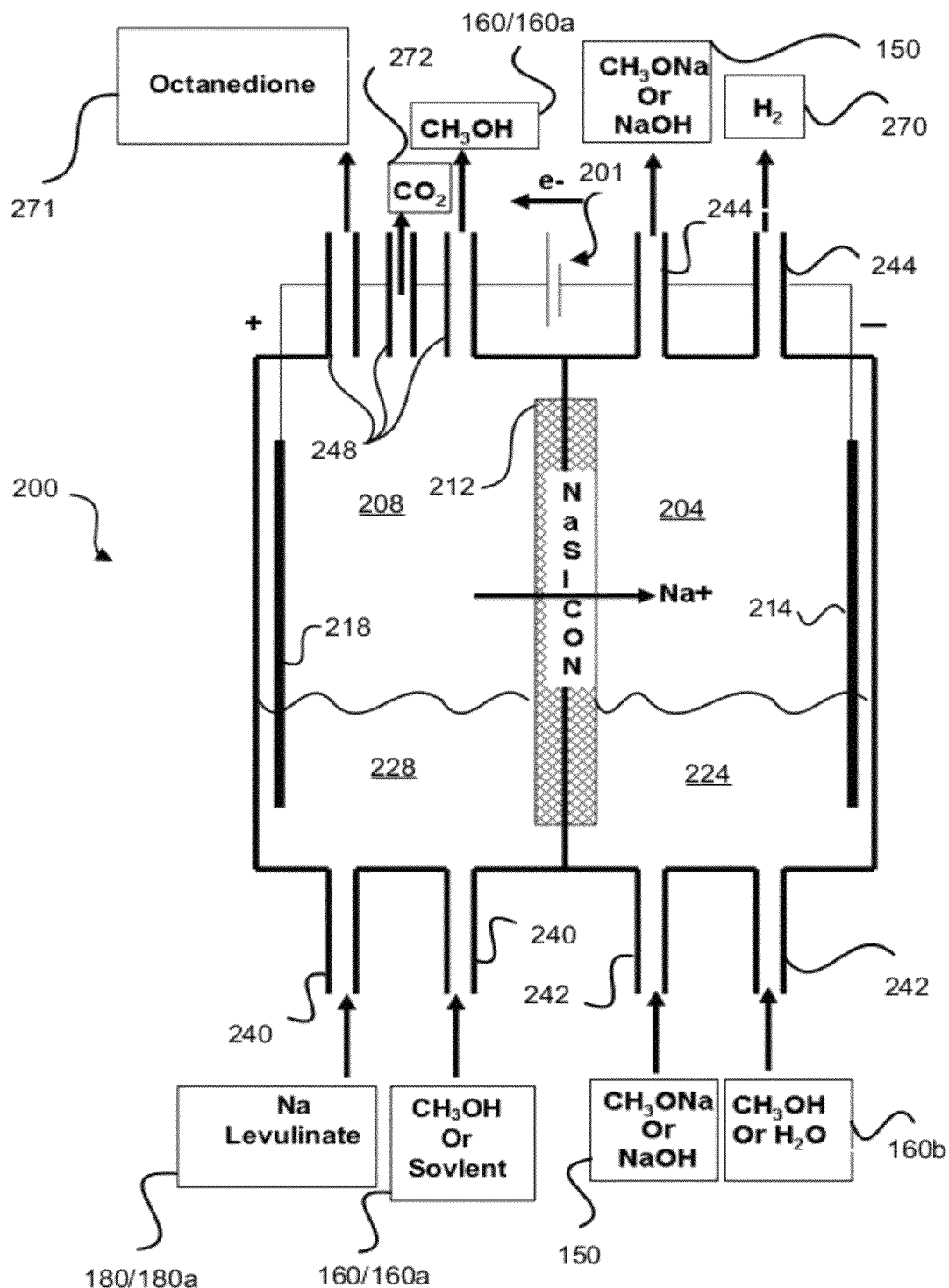
FIG. 3 is a schematic view of an embodiment of an electrolytic cell for conversion of sodium levulinate to a hydrocarbon fuel compound.

Referring now to FIG. 3, an electrochemical cell 200 is shown to which a voltage may be applied. The advanced Kolbe reaction discussed above occurs within the electrochemical cell 200. The cell 200 includes a catholyte compartment 204 and an anolyte compartment 208. The catholyte compartment 204 and the anolyte compartment 208 may be separated by a membrane 212. Other embodiments may be designed in which there is only a single compartment that houses both the anode and the cathode.

The particulars of each cell 200 will depend upon the specific embodiment. For example, the cell 200 may be a standard parallel plate cell, where flat plate electrodes and/or flat plate membranes are used. In other embodiments, the cell 200 may be a tubular type cell, where tubular electrodes and/or tubular membranes are used. An electrochemically active anode 218 is housed, at least partially or wholly, within the anolyte compartment 208. More than one anode 218 may also be used. The anode 218 may comprise, for example, a smooth platinum electrode, a stainless steel electrode, or a carbon based electrode. Examples of a typical carbon based electrode include boron doped diamond, glassy carbon, synthetic carbon, Dimensionally Stable Anodes (DSA) and relatives, and/or lead dioxide. Other electrodes may comprise metals and/or alloys of metals, including S·S, Kovar, Inconel/monel. Other electrodes may comprise RuO$_2$—TiO$_2$/Ti, PtO$_x$—PtO$_2$/Ti, IrO$_x$, CO$_3$O$_4$, MnO$_2$, Ta$_2$O$_5$ and other valve metal oxides. In addition, other materials may be used to construct the electrode such as SnO$_2$, Bi$_2$Ru$_2$O$_7$ (BRO), BiSn$_2$O$_7$, noble metals such as platinum, titanium, palladium, and platinum clad titanium, carbon materials such as glassy carbon, BDD, or Hard carbons. Additional embodiments may have RuO$_2$—TiO$_2$, hard vitrems carbon, and/or PbO$_2$. Again, the foregoing serve only as examples of the type of electrodes that may be employed. The cathode compartment 204 includes at least one cathode 214. The cathode 214 is partially or wholly housed within the cathode compartment 204. The material used to construct the cathode 214 may be the same as the material used to construct the anode 218. Other embodiments may be designed in which a different material is used to construct the anode 218 and the cathode 214.

The anolyte compartment 208 is designed to house a quantity of anolyte 228. The catholyte compartment 204 is designed to house a quantity of catholyte 224. In the embodiment of FIG. 3, the anolyte 228 and the catholyte 224 are both liquids, although solid particles and/or gaseous particles may also be included in either the anolyte 228, the catholyte 224, and/or both the anolyte 228 and the catholyte 224.

The anode compartment 208 and the cathode compartment 204 are separated by an alkali metal ion conductive membrane 212. The membrane utilizes a selective alkali metal transport membrane. For example, in the case of sodium, the membrane is a sodium ion conductive membrane 212. The sodium ion conductive solid electrolyte membrane 212 selectively transfers sodium ions (Na$^+$) from the anolyte compartment 208 to the catholyte compartment 204 under the influence of an electrical potential, while preventing the anolyte 228 and the catholyte 224 from mixing. Examples of such solid electrolyte membranes include those based on NaSICON structure, sodium conducting glasses, beta alumina and solid polymeric sodium ion conductors. Such materials are commercially available. NaSICON typically has a relatively high ionic conductivity at room temperature. Alternatively, if the alkali metal is lithium, then a particularly well suited material that may be used to construct an embodiment of the membrane is LiSICON. Alternatively, if the alkali metal is potassium, then a particularly well suited material that may be used to construct an embodiment of the membrane is KSICON.

As noted above, the saponification reaction shown in FIG. 2B (and/or other reactions) are designed to produce a quantity of an alkali metal salt of levulinic acid 180 (e.g., sodium levulinate). This alkali metal salt of a levulinic acid 180 may be separated and/or purified, as needed Likewise, as desired, if the alkali metal salt of levulinic acid 180 comprises a mixture of fatty acid salts, these compounds may be separated. Alternatively, the alkali metal salt of levulinic acid 180 may not be separated and may comprise a mixture of different salts.

The anolyte compartment 208 may include one or more inlets 240 through which the anolyte 228 may be added. Alternatively, the components that make up the anolyte 228 may be separately added to the anolyte compartment 208 via the inlets 240 and allowed to mix in the cell. The anolyte includes a quantity of the alkali metal salt of levulinic acid 180. In the specific embodiment shown, sodium is the alkali metal, so that alkali metal salt of levulinic acid 180 is a sodium salt 180a. The anolyte 228 also includes a first solvent 160, which as noted above, may be an alcohol, such as methyl alcohol 160a. Of course, other types of solvents may also be used.

The catholyte compartment 204 may include one or more inlets 242 through which the catholyte 224 may be added. The catholyte 224 includes a second solvent 160b. The second solvent 160b may be an alcohol or water (or a mixture of alcohol and water). As shown in FIG. 3, the alcohol is methyl alcohol. Significantly, the solvent 160b in the catholyte 224 may not necessarily be the same as the first solvent 160a in the anolyte 228. In some embodiments, the solvents 160a, 160b may be the same. The reason for this is that the membrane 212 isolates the compartments 208, 204 from each other. Thus, the solvents 160a, 160b may be each separately selected for the reactions in each particular compartment (and/or to adjust the solubility of the chemicals in each particular compartment). Thus, the designer of the cell 200 may tailor the solvents 160a, 160b for the reaction occurring in the specific compartment, without having to worry about the solvents mixing and/or the reactions occurring in the other compartment. This is a significant advantage in designing the cell 200. A typical Kolbe reaction only allows for one solvent used in both the anolyte and the catholyte. Accordingly, the use of two separate solvents may be advantageous. In other embodiments, either the first solvent 160a, the second solvent 160b, and/or the first and second solvents 160a, 160b may comprise a mixture of solvents.

The catholyte 224 may also include a base 150. In the embodiment of FIG. 1, the base 150 may be NaOH or sodium methoxide, or a mixture of these chemicals. The base 150 may be the same base 150 as used in the saponification reaction of FIG. 2B. Alternatively, the base may be a different base than that which was used in the saponification reaction.

The reactions that occur at the anode 218 and cathode 214 will now be described. As with all electrochemical cells, such reactions may occur when a voltage is applied to the cell 200 via (source 201).

At the cathode 214, a reduction reaction takes place. This reaction uses sodium ions from the solvent and the solvent to form hydrogen gas 270 as well as an additional quantity of base 150. Using sodium as the alkali metal, the reduction reaction(s) may be written as follows:

$$2Na^+ + 2H_2O + 2e^- \rightarrow 2NaOH + H_2$$

$$2Na^+ + 2CH_3OH + 2e^- \rightarrow 2NaOCH_3 + H_2$$

The hydrogen gas 270 and/or the base 150 may be extracted through outlets 244. The hydrogen gas 270 may be gathered for further processing for use in other reactions, and/or disposed of or sold. The production of the base 150 is a significant advantage because the base 150 that was consumed in the saponification reaction of FIG. 1 is generated in this portion of the cell 200. Thus, the base formed in the cell may be collected and re-used in future saponification reactions (or other chemical processes). As the base may be re-used, the hassle and/or the fees associated with disposing of the base are avoided.

The reactions that occur at the anode 218 may involve decarboxylation. These reactions may involve an advanced Kolbe reaction (which is a free radical reaction) to form a quantity of a product 271 and carbon dioxide 272. The solvent 160/160a may also be recovered and recycled, if desired, back to the inlet 240 for future use.

Using the chemicals of FIGS. 2A and 2B as an example, the oxidation reactions may be written as follows:

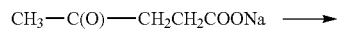
(Sodium levulinate)
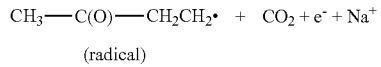
(radical)

The carbon dioxide 272 may be vented off (via one or more outlets 248). This is a safe, naturally-occurring chemical that may be collected, disposed of, or re-used.

The advanced Kolbe reaction may comprise a free radical reaction. As such, the reaction produces (as an intermediate) a radical designated as $CH_3$—$C(O)$—$CH_2CH_2$·. Radical species are highly reactive. Accordingly, when two of these radicals react together, the following product is formed:

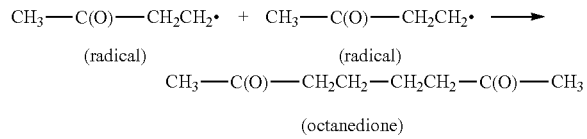
(octanedione)

As shown in FIG. 2, this octanedione makes up the product 271. If the sodium levulinate is purified, then the octanedione may be the predominant product. However, in other embodiments, there may be other products formed in addition to the octanedione. These products may be formed based upon the presence of H radicals, (which are formed from the decarboxylation of formate and/or from hydrogen gas). These H radicals can react with these species (either in a radical reaction or in a hydrogen extraction reaction):

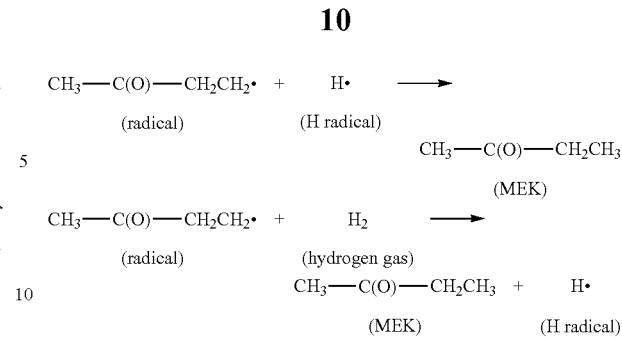

Accordingly, this reaction produces MEK (methyl ethyl ketone), which may be a portion of the product. Additionally, if H radicals (H.) are present in the system, such as from decarboxylation of formate or a hydrogen extraction process, these radicals can react together to form hydrogen gas:

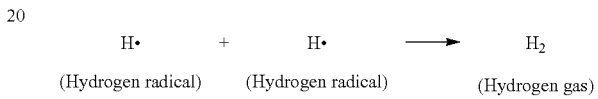

It should be noted that U.S. Provisional Patent Application Ser. No. 61/577,496 includes a variety of different embodiments which disclose various ways to create H. (H radicals) within the reaction cell. (These methods to create H radicals involve photolysis, the use of a Pd catalyst, etc.) As described in this patent application, these H radicals may react to form hydrogen gas, MEK or other products. Those skilled in the art will appreciate that such embodiments that produce H radicals may also be used in conjunction with the present embodiments. However, for purposes of brevity, the description of these methods for forming H radicals will not be repeated.

It should be noted that the embodiments of FIG. 3 are designed in which there are two compartments to the cell. However, those skilled in the art will appreciate that embodiments may be constructed in which there is a single chamber (compartment) in the cell.

It should be noted that the octanedione that is produced in the cell of FIG. 3 may be used as a fuel additive (such as, for example, an additive to gasoline) and/or as a hydrocarbon fuel. Thus, as shown in the present disclosure, the biomass has been converted, using the cell of FIG. 3, into a hydrocarbon fuel.

Figure 4:
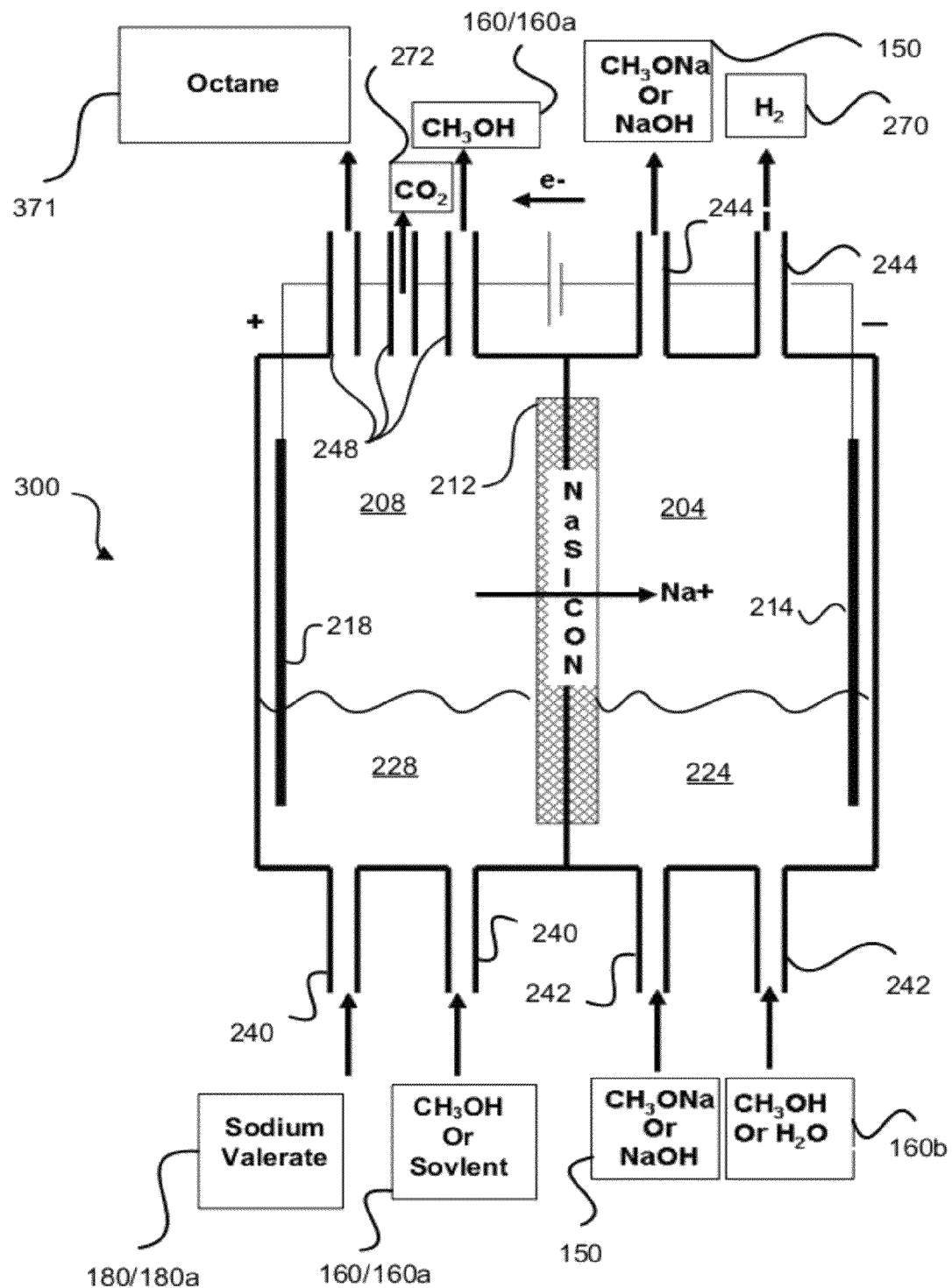
FIG. 4 is a schematic view of an embodiment of an electrolytic cell for conversion of sodium valerate to a hydrocarbon fuel compound.

The above-recited embodiments have been shown using sodium levulinate in the anolyte compartment. However, as noted above, embodiments may also be formed using different starting materials other than sodium levulinate. For example, FIG. 4 shows an embodiment of a cell 300 that is similar to the cell 200 of FIG. 3. However, in the embodiment of FIG. 4, the anolyte comprises sodium valerate instead of sodium levulinate. (The cell 300 is similar to the cell 200 in other aspects, and as such, for purposes of brevity, a repeat description of the features of the cell 300 that similar to that which was described above is omitted.) This sodium valerate may be formed from the biomass. Specifically, as noted above, the hexose sugar may be converted into levulinic acid and formic acid:

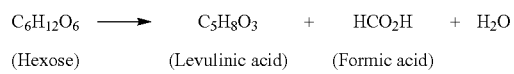

As noted above, the levulinic acid may be reacted to form γ-valerolactone:

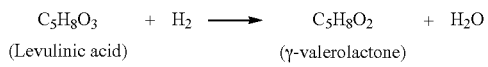

Figure 5:
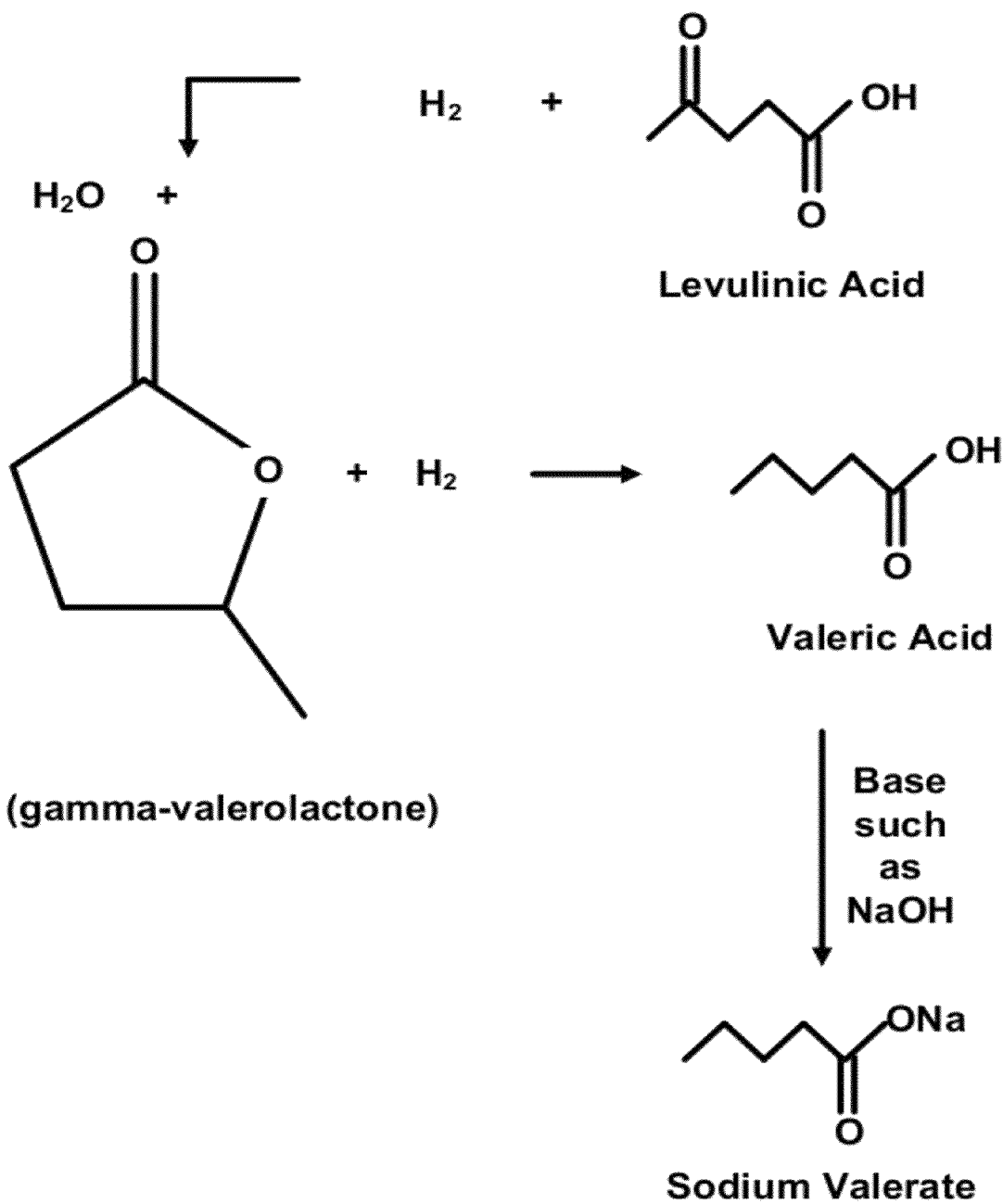
FIG. 5 is a flow diagram showing the conversion of levulinic acid into sodium valerate.

In turn, this γ-valerolactone may further be reacted with hydrogen to form valeric acid ($C_5H_{10}O_2$), as shown by FIG. 5A.

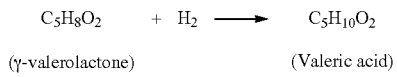

In turn, this valeric acid may be reacted with a base (such as NaOH, $NaOCH_3$, etc.) to form sodium valerate (or another alkali metal valerate). These reactions are shown in FIG. 5B.

This valerate may then be reacted in the cell of FIG. 4 to form octane. More specifically, the valerate 180 (e.g., sodium valerate 180a) will decarboxylate in the cell 300 of FIG. 4 to form the $CH_3$—$CH_2$—$CH_2CH_2$· radical. These two radicals may couple together within the cell to form octane.

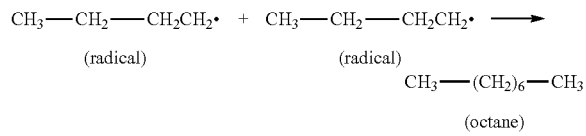

Octane is a valuable hydrocarbon as it is used in gasoline and other fuels. This octane product is shown as product 371 in FIG. 4. Accordingly, by using these embodiments, octane may be formed.

Figure 6A:
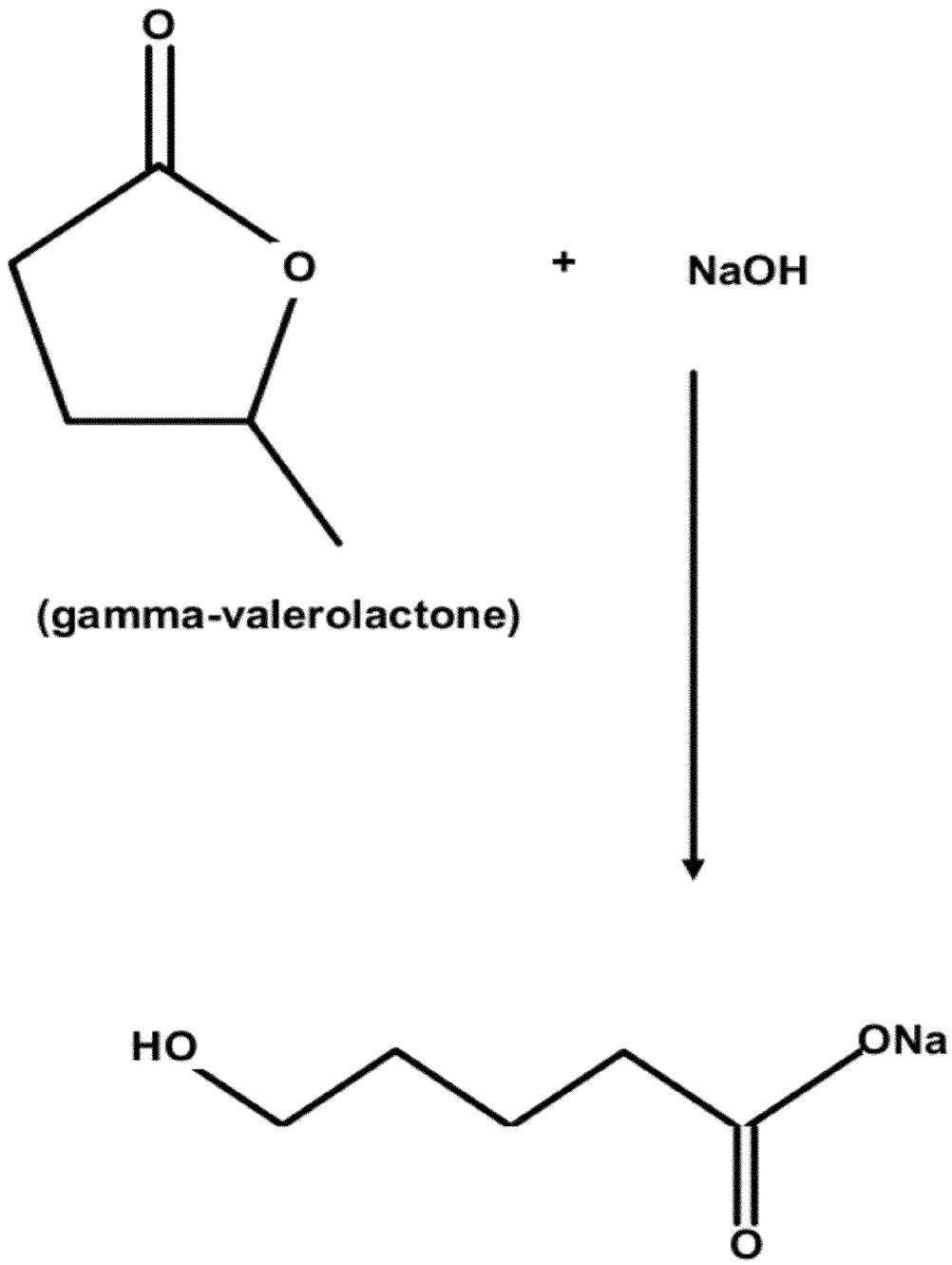
FIG. 6A is a flow diagram showing the conversion of γ-valerolactone into $HO(CH_2)_4COONa$.
Figure 6B:
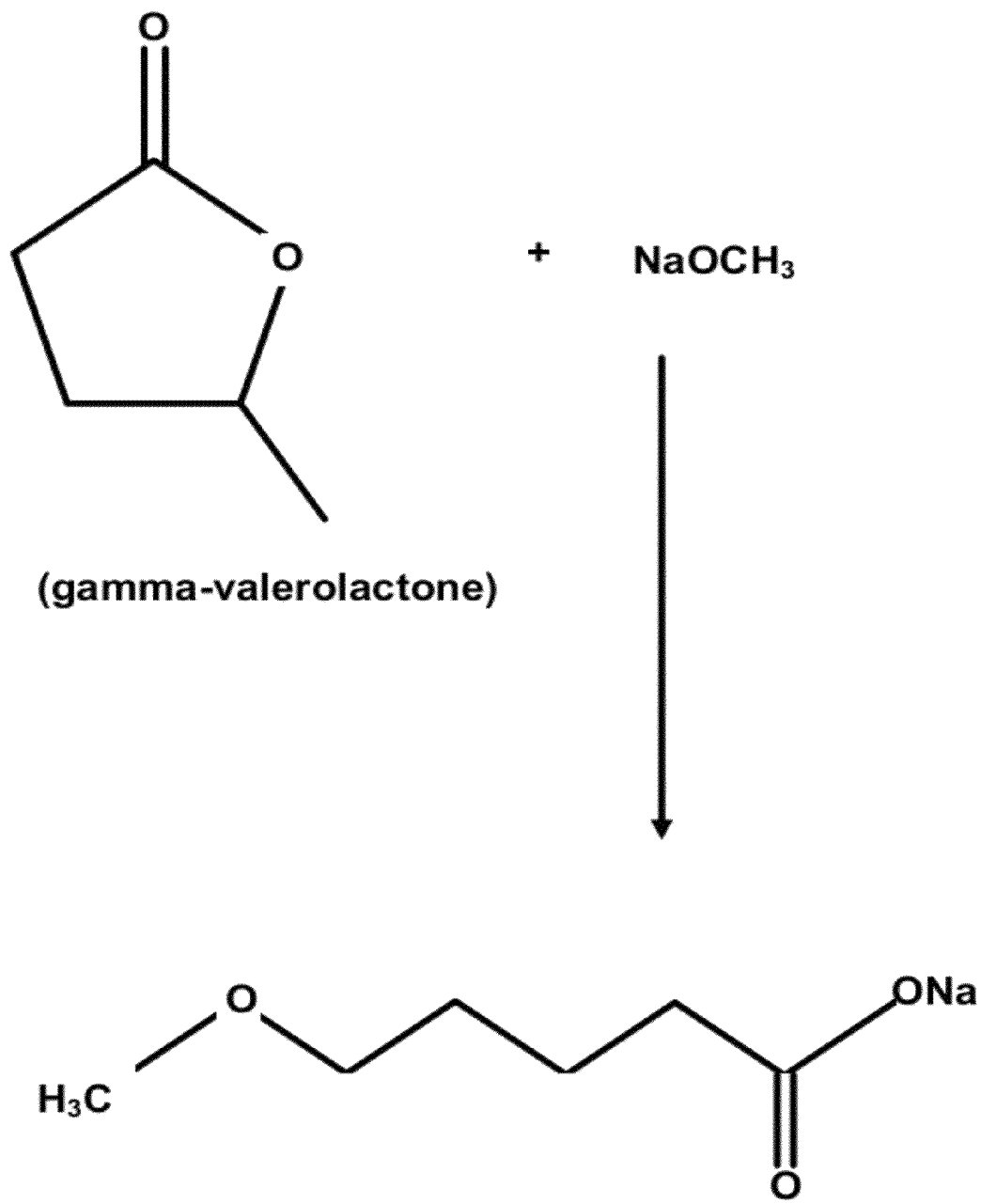
FIG. 6B is a flow diagram showing the conversion of γ-valerolactone into $H_3CO(CH_2)_4COONa$.

Referring now to FIGS. 6A and 6B, the hydrolysis reaction of γ-valerolactone is shown. Specifically, the γ-valerolactone may be reacted with a base. Specifically, FIG. 6A shows the reaction of γ-valerolactone with NaOH whereas FIG. 6B shows the reaction of γ-valerolactone with $NaOCH_3$. Those skilled in the art will appreciate that other bases may also be used in a similar manner. As shown in FIG. 6A, the reaction of γ-valerolactone with NaOH produces $HO(CH_2)_4COONa$. Similarly, as shown in FIG. 6B, the reaction of γ-valerolactone with $NaOCH_3$ produces $CH_3O(CH_2)_4COONa$.

Figure 7:
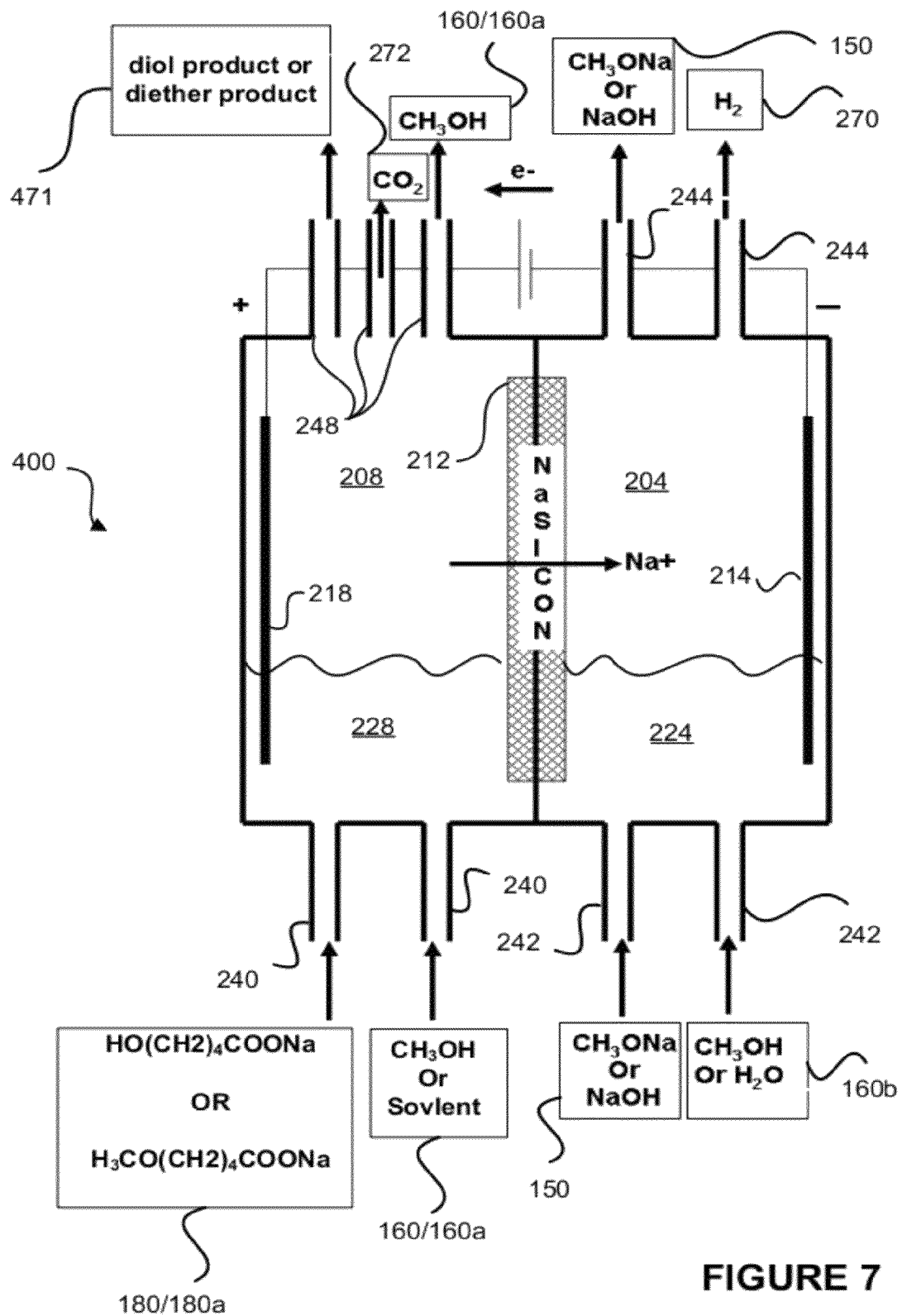
FIG. 7 is a schematic view of yet an embodiment of an electrolytic cell for conversion of $HO(CH_2)_4COONa$ or $H_3CO(CH_2)_4COONa$ into a diol or diether product that may be used as a fuel additive.

As shown in FIG. 7, the species $HO(CH_2)_4COONa$ and/or $CH_3O(CH_2)_4COONa$ may be used in a cell 400 similar to the embodiments discussed herein. (The species $HO(CH_2)_4COONa$ and/or $CH_3O(CH_2)_4COONa$ may be formed using the reactions of FIGS. 6A-6B.) The $HO(CH_2)_4COONa$ and/or $CH_3O(CH_2)_4COONa$ may be added as shown by number 180/180a. (More specifically, element 180a represents a sodium salt of the particular anions whereas element 180 represents a more generic "alkali metal salt" of the anions.) In turn, these species decarboxylate and form the following radicals: $HO(CH_2)_4\cdot$ and $H_3CO(CH_2)_4\cdot$. These radicals may couple as follows:

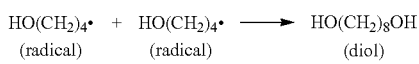

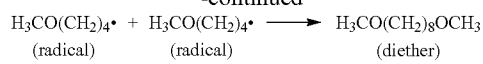

These diol or diether products are shown as product 471 in FIG. 7. Such diol or diether products may be used as additives to gasoline or other fuels.

It should be noted that the cells 200, 300 and 400, outlined herein may have specific advantages. For example, there may be specific advantages associated with using sodium salt of carboxylic acid in the cells 200, 300 and 400, instead of carboxylic acid itself. These advantages include:

R—COONa is more polar than R—COOH and so more probable to decarboxylate at lower voltages;

The electrolyte conductivity may be higher for sodium salts of fatty acids than fatty acids themselves; and/or The anolyte and catholyte can be completely different allowing favorable reactions to take place at either electrode.

Additionally, in the cells 200, 300 and 400, there also may be advantages associated with using sodium ion conductive membranes. For example, the sodium ion conductive solid electrolyte membrane selectively transfers sodium ions ($Na^+$) from the anolyte compartment to the first catholyte compartment under the influence of an electrical potential while preventing anolyte and catholyte mixing. Examples of such solid electrolyte membranes include those based on NaSICON structure, sodium conducting glasses, beta alumina and solid polymeric sodium ion conductors.

Referring now to FIGS. 1-7 collectively, an additional embodiment will be described. Specifically, the present embodiments have been designed to result in a R. (R radical) to R. (R radical) coupling, thereby producing compounds that suitable for use in fuels. Those skilled in the art will appreciate that a second alkali metal carboxylate could be used in conjunction with the compounds described herein and used as part of the anolyte solution. This second carboxylate species may have between 1 to 7 carbon atoms. The use of this second carboyxlate may have some advantages such as:

The second carboxylate can act as a suitable supporting electrolyte providing high electrolyte conductivity;

The second carboxylate will itself decarboxylate and produces alkyl radicals by the following reaction:

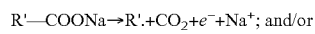

The second alkyl radical can then be reacted with radicals formed from first sodium carboxylate (from sodium levulinate or sodium valerate or the base hydrolysis products of γ-valerolactone) to form hydrocarbons with additional $CH_3$— (or other alkyl) functional groups:

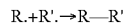

The R—R' product can be a hydrocarbon that has number of carbon atoms in the range of diesel fuel or diesel fuel additive.

Figure 8:
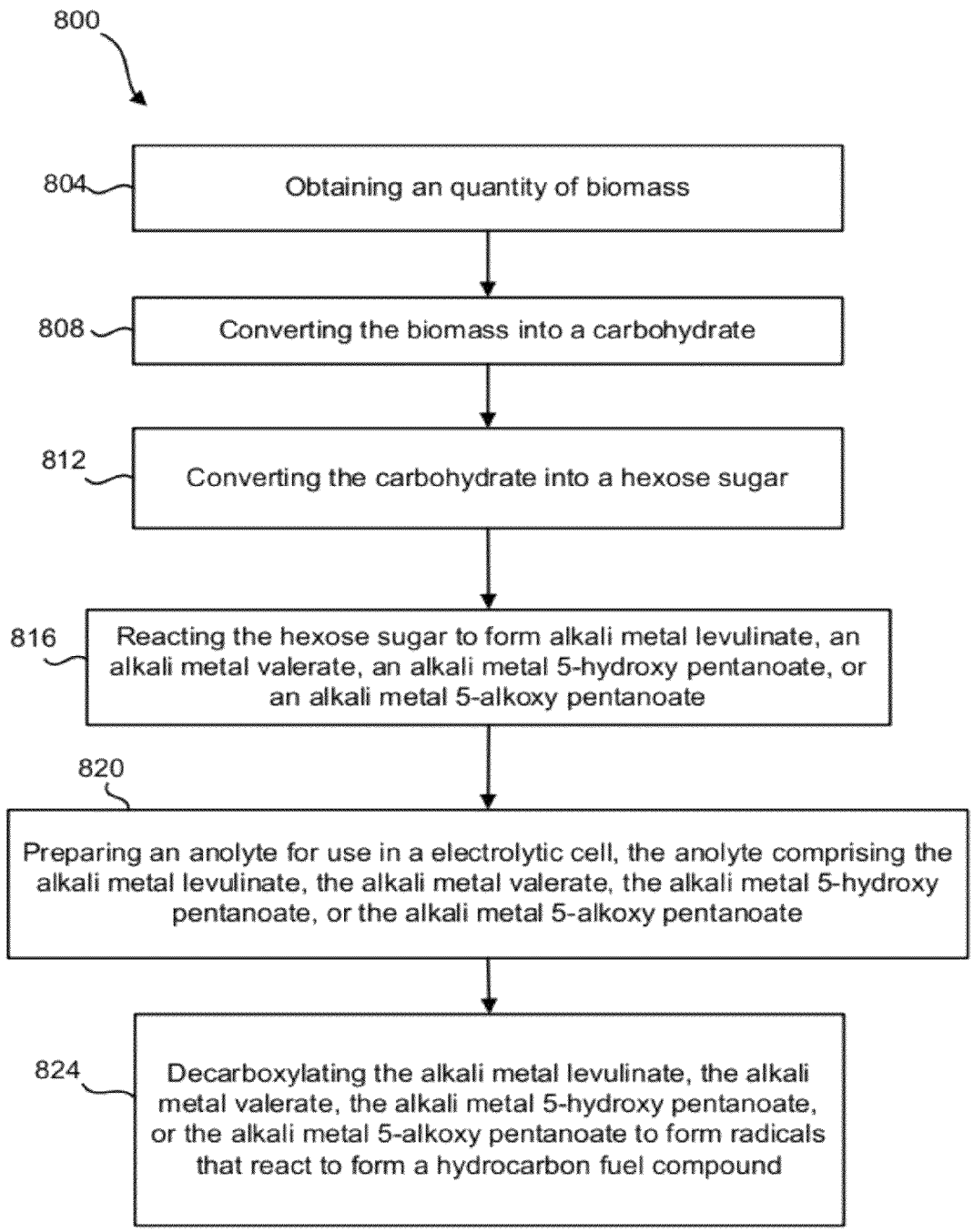
FIG. 8 is a flow diagram showing an exemplary method of the present embodiments.

Referring now to FIG. 8, a flow diagram is shown of a method 800 for producing a hydrocarbon fuel compound. The method 800 comprises obtaining 804 quantity of biomass. As noted above, this biomass may be from plant, animal, algal, or other sources. This biomass may then be converted 808 into a carbohydrate. The carbohydrate may be converted 812 into a hexose sugar. As described herein, the hexose sugar may then be reacted to form an alkali metal levulinate, an alkali metal valerate, an alkali metal 5-hydroxy pentanoate ($HO(CH_2)_4COONa$), or an alkali metal 5-alkoxy pentanoate ($RO(CH_2)_4COONa$, where "R" is an alkyl group such as methyl, ethyl, butyl, propyl, isopropyl, or any desired alkyl group). The methods for forming these compounds are described above. Alternatively, the alkali metal levulinate, alkali metal valerate, alkali metal 5-hydroxy pentanoate (HO(CH$_2$)$_4$COONa), or alkali metal 5-alkoxy pentanoate may be purchased or otherwise obtained.

As noted herein, this alkali metal levulinate, alkali metal valerate, alkali metal 5-hydroxy pentanoate, or alkali metal 5-alkoxy pentanoate may be added 820 to an anolyte. Once prepared, the anolyte may be placed in the electrolytic cell. The alkali metal levulinate, alkali metal valerate, alkali metal 5-hydroxy pentanoate, or alkali metal 5-alkoxy pentanoate may then be decarboxylated 824 in the electrolytic cell. This decarboxylation operates to convert the alkali metal levulinate, alkali metal valerate, alkali metal 5-hydroxy pentanoate, or alkali metal 5-alkoxy pentanoate into radicals that may react to form a hydrocarbon fuel product. For example, if the material is an alkali metal levulinate, the radicals may react (couple) to form 2,7-octadione (which may be a gasoline additive). If the material is an alkali metal valerate, the radicals may react (couple) to form octane. If the material is alkali metal 5-alkoxy pentanoate, the radicals may react (couple) to form 1,8-dialkoxy octane. If the material is an alkali metal 5-hydroxy pentanoate the radicals may react (couple) to form 1,8-hydroxy octane.

Figure 9:
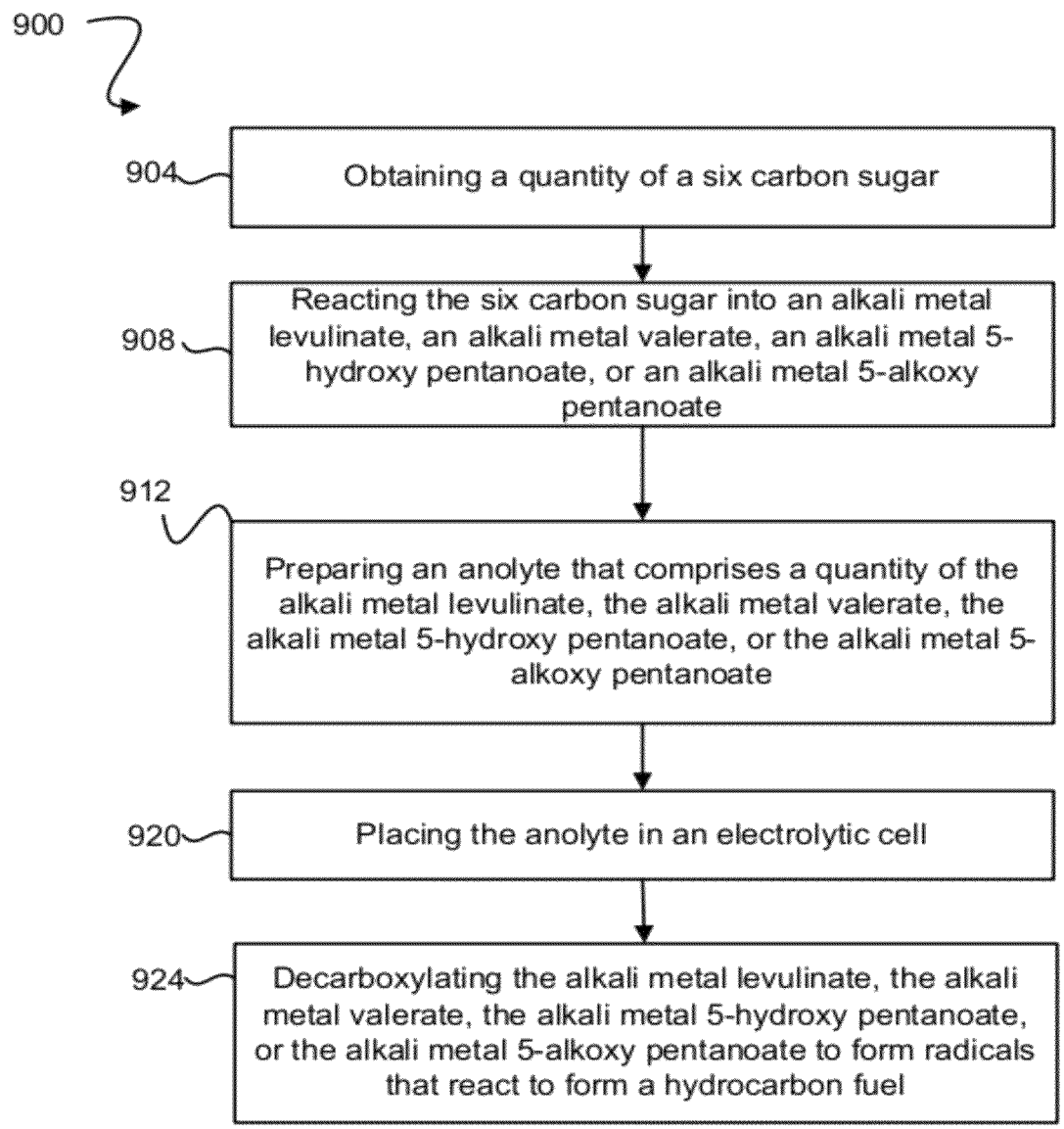
FIG. 9 is another flow diagram showing another exemplary method of the present embodiments.

Referring now to FIG. 9, another exemplary method 900 according to the present embodiments is illustrated. The method 900 may be used to form hydrocarbon fuel compound. The method involves obtaining 904 a quantity of a six carbon sugar. Once obtained, the six carbon sugar is reacted 908 into an alkali metal levulinate, an alkali metal valerate, an alkali metal 5-hydroxy pentanoate, or an alkali metal 5-alkoxy pentanoate.

An anolyte will then be prepared 912. The anolyte comprises a quantity of the alkali metal levulinate, the alkali metal valerate, the alkali metal 5-hydroxy pentanoate, or the alkali metal 5-alkoxy pentanoate. Once prepared, the anolyte may be placed 920 in an electrolytic cell, such as those described herein.

After placing the anolyte in the cell, the alkali metal levulinate, the alkali metal valerate, the alkali metal 5-hydroxy pentanoate, or the alkali metal 5-alkoxy pentanoate is decarboxylated 924. This decarboxylation may involve electrolysis. Such decarboxylation forms one or more radicals that react to form a hydrocarbon fuel product such as, for example, octane, octadione, 1,8-hydroxy octane, and/or 1,8-dialkoxy octane.

EXAMPLES

Tests were run in order to test the decarboxylation of products. In order to perform this testing, an electrochemical cell was prepared. This cell consisted of a two compartment electrochemical cell with minimal membrane-anode gap. The minimal gap is necessary for creating optimum mass transfer conditions in the anolyte compartment. A smooth platinum anode was used where decarboxylation occurs. A 1" (one inch) diameter and 1 mm thick NaSICON ceramic membrane was used between the anode and cathode compartment. The NaSICON membrane was obtained from the Ceramatec company of Salt Lake City, Utah. A nickel cathode was used in the cathode compartment.

The test set up consisted of 1 liter glass flasks sealed with 3 holed rubber stoppers as anolyte and catholyte reservoirs. Each reservoir was placed on a hot plate and thermocouples were placed in each of the reservoirs. About 300 mL of anolyte (18.6% (wt/wt) sodium levulinate in methanol) and catholyte (15 wt. % aqueous NaOH) were used. The temperature was controlled by a temperature controller to maintain the temperature of feed solutions to the anolyte, and catholyte at 45° C. Pumps were used to circulate the anolyte and catholyte solutions.

Figure 10:
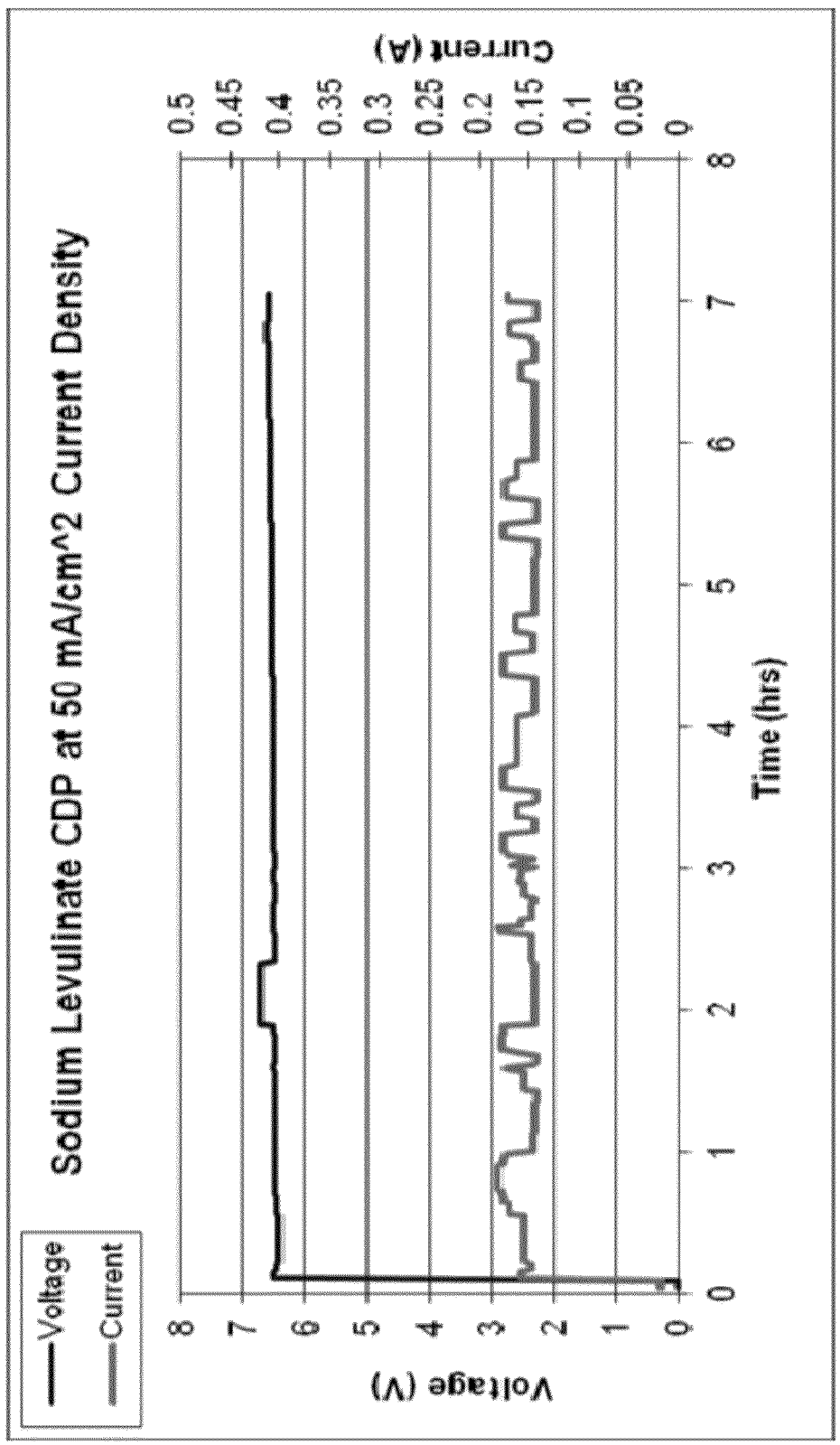
FIG. 10 shows a graph of current density and voltage for an example decarboxylation process.

Test Summary:

Electrochemical decarboxylation was conducted at a current density of ~50 mA per cm$^2$ of membrane area for 7 hours. The cell was operated until 20%(wt/wt) of the starting available sodium content was removed. The voltage profile for this constant current test data is shown in FIG. 10. The voltage stayed constant during the sodium removal and decarboxylation process.

Figure 11:
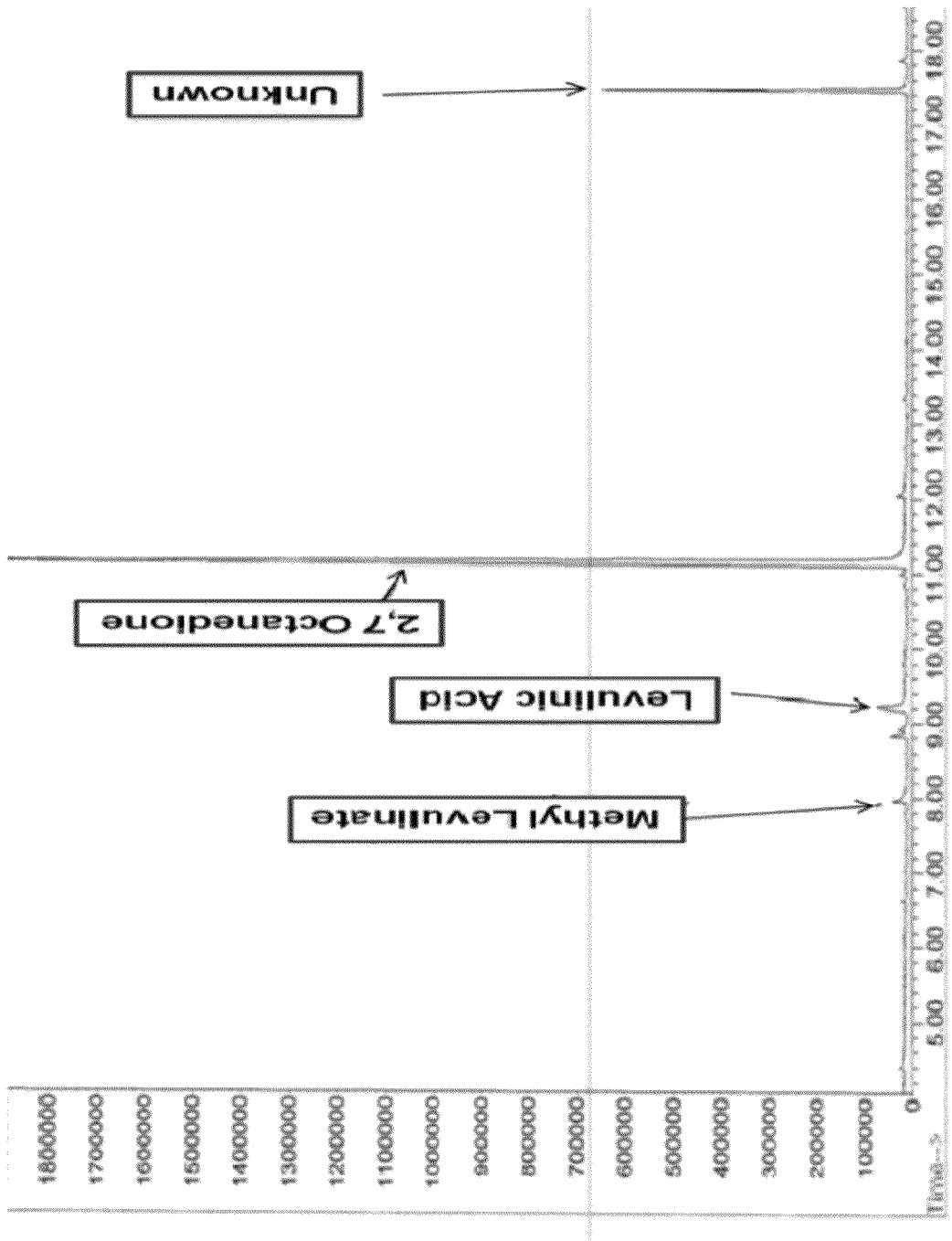
FIG. 11 shows a gas chromatogram of a decarboxylation process that was performed.

Results:

The post-reaction anolyte solution was analyzed by GC-MS analysis. 2,7-octanedione was the predominant product along with a minor unknown bi-product and traces of methyl levulinate and levulinic acid. The GC chromatogram is shown as FIG. 11.

All of the articles/papers mentioned in this disclosure are expressly incorporated herein by reference.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method for producing a hydrocarbon fuel compound comprising:
    obtaining sodium levulinate, wherein the sodium levulinate is derived from a six carbon sugar;
    preparing an anolyte for use in an electrolytic cell, the electrolytic cell comprising an anolyte compartment, a catholyte compartment, and a NaSICON membrane that separates the anolyte compartment from the catholyte compartment, wherein the anolyte is housed within the anolyte compartment and a catholyte is housed within the catholyte compartment, wherein the anolyte comprises a solvent and a quantity of the sodium levulinate, wherein the solvent comprises an alcohol; and
    electrolyzing the anolyte within the cell, wherein the electrolyzing decarboxylates the sodium levulinate to form radicals, wherein the radicals react to predominantly form 2,7-octadione,
    wherein the quantity of the sodium levulinate is devoid of levulinic acid, wherein the only positive cation in the anolyte compartment is the sodium cation.

2. A method as claimed in claim 1, wherein the 2,7-octadione is a gasoline additive.

3. A method as in claim 1, wherein the alcohol comprises methanol.

4. A method as in claim 1, wherein obtaining sodium levulinate comprises reacting levulinic acid with a base comprising either NaOH or NaOCH$_3$.

5. A method as in claim 4, wherein the cathode compartment regenerates the base that was used to react with the levulinic acid.

6. A method as in claim 5, wherein the alcohol comprises methanol.

* * * * *